US010675855B2

(12) United States Patent
Zachariasen et al.

(10) Patent No.: US 10,675,855 B2
(45) Date of Patent: *Jun. 9, 2020

(54) USE OF ADDITIVE MANUFACTURING PROCESSES IN THE MANUFACTURE OF CUSTOM WEARABLE AND/OR IMPLANTABLE MEDICAL DEVICES

(71) Applicant: 3D Patents, LLC, Mesa, AZ (US)

(72) Inventors: Joseph T. Zachariasen, Medford, OR (US); Dean E. Cropper, Talent, OR (US)

(73) Assignee: 3D Patents, LLC, Mesa, AZ (US)

( * ) Notice: Subject to any disclaimer, the term of this patent is extended or adjusted under 35 U.S.C. 154(b) by 615 days.

This patent is subject to a terminal disclaimer.

(21) Appl. No.: 15/297,092

(22) Filed: Oct. 18, 2016

(65) Prior Publication Data
US 2017/0036402 A1 Feb. 9, 2017

Related U.S. Application Data

(63) Continuation of application No. 14/808,203, filed on Jul. 24, 2015, now Pat. No. 9,469,075, which is a
(Continued)

(51) Int. Cl.
*B33Y 30/00* (2015.01)
*A61F 2/66* (2006.01)
(Continued)

(52) U.S. Cl.
CPC ............ *B33Y 30/00* (2014.12); *A61F 2/6607* (2013.01); *A61F 5/01* (2013.01); *A61F 5/0127* (2013.01);
(Continued)

(58) Field of Classification Search
CPC ............ A61F 5/0127; A61F 2240/002; A61F 2240/004; A61F 5/01; B29C 64/00;
(Continued)

(56) References Cited

U.S. PATENT DOCUMENTS 5,432,703 A 7/1995 Clynch et al.
6,141,889 A 11/2000 Baum
(Continued)

FOREIGN PATENT DOCUMENTS

GB 2508204 A 5/2014
WO 2014080217 A1 5/2014

OTHER PUBLICATIONS

USPTO as International Searching Authority "International Search Report and Written Opinion," International Application No. PCT/US2013/077589, dated Mar. 19, 2014.
(Continued)

*Primary Examiner* — Anna K Kinsaul
*Assistant Examiner* — Caitlin A Carreiro
(74) *Attorney, Agent, or Firm* — Durham Jones & Pinegar, P.C.

(57) ABSTRACT

A method for manufacturing a custom wearable and/or implantable medical device, such as an orthosis (e.g., an ankle brace, etc.), a prosthesis or the like, includes use of scanning processes. A digital model of a surface may be applied to a digital device model to define a custom digital device model. The digital model and, thus, the custom digital device model may include one or more standard features. The custom digital device model may be used with an automated manufacturing process to make some or all of the custom wearable and/or implantable medical device. In some embodiments, additive manufacturing processes may be used to form a portion or all of the custom wearable and/or implantable medical device.

20 Claims, 4 Drawing Sheets

Related U.S. Application Data continuation-in-part of application No. 14/139,489, filed on Dec. 23, 2013, now Pat. No. 9,610,731.

(60) Provisional application No. 61/800,582, filed on Mar. 15, 2013, provisional application No. 61/745,557, filed on Dec. 22, 2012.

(51) Int. Cl.
| | |
|---|---|
| *G05B 19/4099* | (2006.01) |
| *B33Y 50/02* | (2015.01) |
| *A61F 5/01* | (2006.01) |
| *B33Y 80/00* | (2015.01) |
| *B33Y 10/00* | (2015.01) |
| *B29L 31/00* | (2006.01) |
| *G06F 17/50* | (2006.01) |
| *B29C 64/00* | (2017.01) |
| *B29C 64/20* | (2017.01) |
| *B29C 64/386* | (2017.01) |

(52) U.S. Cl.
CPC ............. *B29C 64/00* (2017.08); *B29C 64/20* (2017.08); *B29C 64/386* (2017.08); *B33Y 10/00* (2014.12); *B33Y 50/02* (2014.12); *B33Y 80/00* (2014.12); *G05B 19/4099* (2013.01); *G06F 17/5086* (2013.01); *A61F 2240/002* (2013.01); *A61F 2240/004* (2013.01); *B29L 2031/7532* (2013.01); *G06F 17/50* (2013.01)

(58) Field of Classification Search
CPC ............. B29C 64/386; B29C 67/0051; B29L 2031/7532; B33Y 10/00; B33Y 30/00; G06F 17/50
USPC ............. 602/5–8, 20–28; 328/128; 382/128
See application file for complete search history.

(56) References Cited

U.S. PATENT DOCUMENTS

| | | | |
|---|---|---|---|
| 6,402,713 | B1 | 6/2002 | Doyle |
| 6,463,351 | B1 | 10/2002 | Clynch |
| 8,409,122 | B2 | 4/2013 | Cropper et al. |
| 8,538,570 | B2 | 9/2013 | Stanhope et al. |
| 8,838,263 | B2 | 9/2014 | Sivak et al. |
| 9,469,075 | B2 * | 10/2016 | Zachariasen .......... A61F 2/6607 |
| 9,610,731 | B2 | 4/2017 | Zachariasen |
| 2002/0010408 | A1 | 1/2002 | Pomatto et al. |
| 2007/0016323 | A1 | 1/2007 | Fried |
| 2007/0118243 | A1 | 5/2007 | Schroeder et al. |
| 2007/0133850 | A1 | 6/2007 | Paez |
| 2008/0292179 | A1 | 11/2008 | Busch |
| 2009/0306801 | A1 | 12/2009 | Sivak et al. |
| 2010/0094174 | A1 | 4/2010 | Choi et al. |
| 2010/0113980 | A1 | 5/2010 | Herr et al. |
| 2010/0262054 | A1 | 10/2010 | Summit et al. |
| 2011/0009787 | A1 | 1/2011 | Pallari et al. |
| 2011/0082578 | A1 | 4/2011 | Stanhope et al. |

OTHER PUBLICATIONS

Berry, E., et al., "Preliminary experience with medical applications of rapid prototyping by selective laser sintering," Med. Eng. Phys., 19(1):90-96 (1997).

Darling, AL, et al., "Orthotic design through 3D reconstruction: A passive-assistance ankle-foot orthotic," Appl. Bion. Biomech., 3(2):93-99 (2006).

Dean, D., et al., "Computer Aided Design of Large-Format Prefabricated Cranial Plates," J. Craniofac. Surg., 14 (6):819-32 (Nov. 2003).

Faustini, MC, et al., "Manufacture of Passive Dynamic Ankle-Foot Orthoses Using Selective Laser Sintering," IEEE Trans. Biomed. Eng., 55(2 pt. 1):784-90 (Feb. 2008).

\* cited by examiner

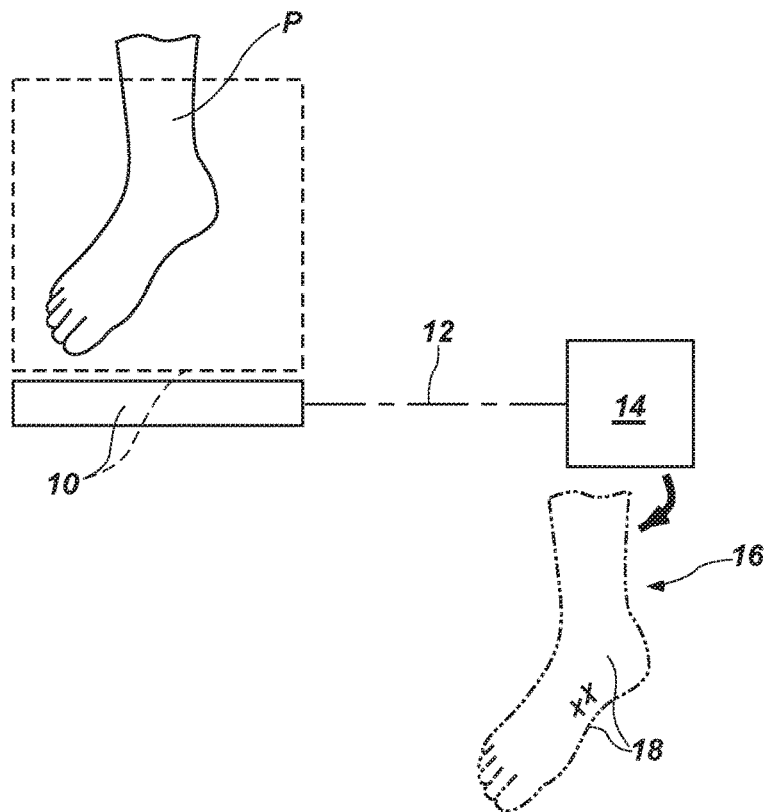
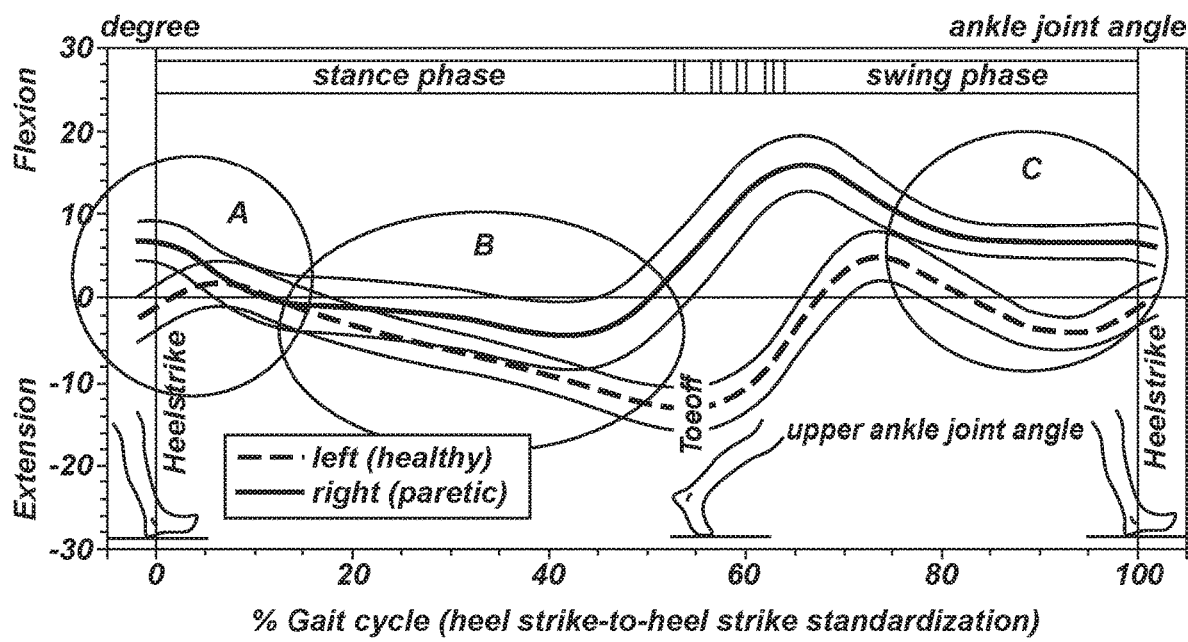

USE OF ADDITIVE MANUFACTURING PROCESSES IN THE MANUFACTURE OF CUSTOM WEARABLE AND/OR IMPLANTABLE MEDICAL DEVICES

CROSS-REFERENCE TO RELATED APPLICATIONS

This application is a continuation of U.S. patent application Ser. No. 14/808,203, filed on Jul. 24, 2015 and titled USE OF ADDITIVE MANUFACTURING PROCESSES IN THE MANUFACTURE OF CUSTOM WEARABLE AND/OR IMPLANTABLE MEDICAL DEVICES ("the '203 Application"), now U.S. Pat. No. 9,469,075, issued on Oct. 18, 2016, which is a continuation-in-part of U.S. patent application Ser. No. 14/139,489, filed on Dec. 23, 2013 and titled USE OF ADDITIVE MANUFACTURING PROCESSES IN THE MANUFACTURE OF CUSTOM ORTHOSES ("the '489 Application"), now U.S. Pat. No. 9,610,731, issued on Apr. 4, 2017. The '489 Application included claims for priority under 35 U.S.C. § 119(e) to the Dec. 22, 2012 filing date of U.S. Provisional Patent Application No. 61/745,557, titled USE OF ADDITIVE MANUFACTURING PROCESSES IN THE MANUFACTURE OF CUSTOM ORTHOSES, ("the '557 Provisional Application") and to the Mar. 15, 2013 filing date of U.S. Provisional Patent Application No. 61/800,582, also titled USE OF ADDITIVE MANUFACTURING PROCESSES IN THE MANUFACTURE OF CUSTOM ORTHOSES, ("the '582 Provisional Application"). The entire disclosures of the '203 Application, the '489 Application, the '557 Provisional Application and the '582 Provisional Application are hereby incorporated herein.

TECHNICAL FIELD

This disclosure relates generally to methods for manufacturing custom wearable and/or implantable medical devices, such as custom orthoses (e.g., braces, etc.) and custom prostheses that are configured to be secured to an exterior of a subject's body, and, more specifically, to the use of additive manufacturing processes to manufacture custom wearable and/or implantable medical devices. In addition, this disclosure relates to systems that employ scanning or digitizing equipment and additive manufacturing equipment in the manufacture of custom wearable and/or implantable medical devices, and to custom wearable and/or implantable medical devices that include one or more components that have been fabricated by additive manufacturing processes.

RELATED ART

Custom orthoses, such as braces (e.g., knee braces, ankle braces, etc.), and custom prosthetic devices are typically designed to specifically fit the individual for whom they are customized. Customization of an orthosis may optimize the support that the orthosis provides to a body part, such as a joint, to which the orthosis has been fitted. In addition, custom orthoses are typically more comfortable than and provide for increased function and therapy over standard versions of the same types of orthoses, including sized orthoses. Customization of a prosthesis may ensure that the prosthesis properly fits a residual limb (i.e., a stump) or other residual body part next to which the prosthesis is to be secured, which may ensure that the prosthesis may be securely coupled to a subject's body, minimize injury to the subject's body, and make the prosthesis as comfortable as possible for the subject to wear.

Conventionally, custom orthoses have been made by casting a negative mold of the part of an individual's body that an orthosis is supposed to support. The negative mold is then sent to the orthosis manufacturer, who uses the negative mold to make a positive mold, which generally serves as an accurate replica of the individual's body part. Depending at least partially upon the type of orthosis being made, the material may be added to or removed from the positive mold. One or more customized features of the orthosis may then be made on the positive mold, often by hand. From the forgoing, it should be apparent that conventional processes for making custom orthoses are labor intensive and time consuming.

The interface (e.g., socket, cup, etc.) of a custom prosthesis may also be molded to the part of a subject's body (e.g., a residual limb, etc.) to which the interface is to be secured. Such molding may be conducted in a manner similar to the way in which conventional custom orthoses have been have been made. Additionally, custom prostheses may be fabricated to match an opposite body part (e.g., the other limb, etc.) to balance function and aesthetics.

U.S. Pat. No. 6,155,997 to Castro (hereinafter "Castro") discloses an improvement upon the conventional process for making custom orthoses. Specifically, Castro discloses processes for making custom ankle braces. According to Castro, one enhancement to the conventional process for making custom orthoses includes the application of instructions, in the form of readily recognizable symbols, to an inner surface of a negative mold. The instructions may be placed on the inner surface of the negative mold by a person, such as a health care professional, who is prescribing the custom ankle brace. When the brace maker receives the negative mold and uses it to create a positive mold, the instructive symbols that were placed on the inner surface of the negative mold are transferred to corresponding locations on an outer surface of the positive mold. The brace maker may then follow the instructions conveyed by the symbols to define features of (e.g., build them up on, remove material from, etc.) the positive mold. Once the brace maker has modified the positive mold in accordance with the instructions conveyed by the symbols, he or she may use the positive mold to make a custom ankle brace. Like other parts of the process, custom ankle braces are also usually made by hand.

Because conventional processes for making custom orthoses (e.g., custom ankle braces, customized portions of knee braces, etc.) and custom interfaces for externally worn prostheses may be very labor-intensive, such processes, from casting of a negative mold to completion of the custom orthosis or custom prosthesis, typically take an inordinate amount of time (e.g., weeks, a month, etc.) to complete. Thus, an individual for whom the orthosis or prosthesis is being made, and who may rely on that orthosis or prosthesis, may have to live without the orthosis or the prosthesis for the same amount of time.

SUMMARY

A process for making a custom wearable and/or implantable medical device, such as a custom orthosis or a custom prosthesis (which may be detachable, surgically attached, etc.), according to this disclosure includes the generation of a three-dimensional digital model (e.g., a computer-aided design (CAD) file, etc.) that represents a negative (e.g., a casting, etc.) of a body part for which the orthosis or the prosthesis is being made. For the sake of simplicity, the negative three-dimensional digital model may also be referred to herein as a "digital body model" or, even more simply, as a "body model." The body model may serve as the basis for a digital device model or for a digital prosthesis model, which may be used in conjunction with an additive manufacturing process to make the custom orthosis or the custom prosthesis, or at least a customized portion of an orthosis or a customized portion of a prosthesis.

As used hereinafter, "custom orthosis" may refer to an orthosis that has been customized for use with a body part of a particular individual, to a customized portion of an orthosis, or to both the entire orthosis and a customized feature thereof. Similarly, the term "orthosis" may be used in reference to an entire orthosis, a part of an orthosis that is (or is to be) customized, or to both the entire orthosis and any part thereof that may be customized.

The term "custom prosthesis," as used hereinafter, may refer to an externally wearable prosthesis that has been customized for use with a body part of a particular individual, to a customized portion (e.g., an interface, etc.) of a prosthesis, or to both the entire prosthesis and a customized feature thereof. The term "prosthesis" may refer to an entire externally wearable prosthesis (e.g., a daily wear prosthesis, a prosthesis that is permanently affixed to the body, etc.), to a part of the prosthesis that is (or is to be) customized, or to both the entire prosthesis and any part thereof that may be customized. Such a prosthesis may be configured to be readily attached to and/or removed from a subject's body. The term "custom prosthesis," as used herein, may also refer to a surgically attachable prosthesis. A surgically attachable prosthesis may be configured to be surgically attached to an exterior location of a subject's body, to be attached within a subject's body while including one or more elements that are externally located and/or accessible from outside of the subject's body or to be surgically attached and wholly remain within a subject's body. Some non-limiting examples of surgically implantable prostheses include bones, joints, cartilage, ligaments, tendons, muscles and a variety of other organs, including, but not limited to, artificial hearts, artificial kidneys, artificial livers and artificial pancreases. A custom prosthesis may comprise a passive, or stationary, structure or it may include one or more movable elements and, in some embodiments, may itself be movable.

The body model may be generated by digitizing or scanning (e.g., a three-dimensional scan; a three-dimensional, multi-point analysis from which a three-dimensional model may be extrapolated; a two-dimensional scan that can be used to generate a three-dimensional model; etc.) of the body part for which the orthosis or the prosthesis is being made or with which the orthosis or the prosthesis will interface. As used herein, the terms "scan," "scanning," "scanner," and similar terms relate to techniques for obtaining three or more data points from which a three-dimensional model may be generated, including scanning techniques and digitizing techniques. Thus, the results of scanning a body part may be used to generate a three-dimensional digital model of the body part, which is also referred to herein as a "body part digital model" or as a "body part model." The body part model may then provide a basis for generation of a negative model of the body part, which comprises a digital negative model of the body part, or a digital body model, which serves as the basis for the contour of one or more surfaces of an orthosis, a prosthesis, or another medical device.

In some embodiments where digitization or scanning is used to generate a digital body model, a body part may be scanned while it is in two or more positions. Such scanning, which is also referred to herein as "dynamic scanning," may be accomplished by incrementally positioning the body part in (and optionally between) the two or more positions. As an example, a foot, ankle, and/or knee may be scanned while the body part is placed in two or more positions that typically occur as a subject walks (e.g., heel strike, mid-gait, toe-off, etc.). A scan may then be obtained with the body part in each of the incremental positions. Alternatively, the body part may be scanned and two or more images obtained during movement of the body part; for example, while the subject walks (e.g., through at least one cycle of heel strike, mid-gait and toe-off, etc.). A dynamic scan may provide information about how motion of an impaired (e.g., injured, defective, etc.) body part (i.e., unnatural motion) varies from natural motion for that body part. That information may be used to generate a model for a custom orthosis that prevents, or blocks out, unnatural motion while allowing or, or even enabling, desired motion (e.g., natural motion, etc.), which facilitates correction of the impairment to the body part.

In embodiments where a custom prosthesis is being made, dynamic scanning may be used to provide information about movement of a residual body part (e.g., a residual limb, etc.) while the residual body part and a prosthesis secured thereto are moved. Dynamic scanning may provide information about interaction (e.g., movement, etc.) between the residual body part and the prosthesis (e.g., an interface of a non-custom prosthesis, etc.).

During the healing processes, gait and/or other body dynamics may change. These changes may be identified and documented by dynamic scanning. Accordingly, by repeating the dynamic scanning process during the healing process (e.g., periodically, as an individual's condition changes, etc.), information may be obtained which may be used to adapt a wearable and/or implantable medical device, such as an orthosis or a prosthesis, to an individual's new needs. By way of example, the information obtained by repeating the dynamic scanning process may be used to fabricate a new custom wearable and/or implantable medical device. As another example, information obtained during repeated dynamic scanning may be used to modify an existing orthosis, prosthesis, or other wearable and/or implantable medical device (e.g., by enabling the fabrication of a newly customized modular, updatable part that may be assembled with a remainder of the orthosis, prosthesis, or other wearable and/or implantable medical device, etc.).

As an alternative to generating a body model from digitized data, a body model may be generated from a negative mold of the body part (e.g., by scanning the negative mold, etc.). In embodiments where a negative mold serves as the basis for the three-dimensional digital model, the negative mold may be made by, or at least ordered by, a health care professional. One or more readily recognizable, optionally standardized symbols or other indicia may be placed at locations where the orthosis is to be modified (e.g., built up, etc.) in a manner prescribed by the health care professional ordering the orthosis or other medical device. Those indicia may convey information for subsequent use by an individual (manual) or computer (automated) while generating a digital device model from data obtained from the negative mold. Negative molds are particularly useful in situations in which a scanner is not readily available to the health care professional. In those situations, and under other circumstances, the negative mold may be sent to a facility, such as a custom orthosis manufacturer or a custom prosthesis manufacturer, where the negative mold can be scanned to generate the negative model.

As another alternative, a positive physical model of a body part may be used as the basis for the body model. The positive physical model may be made by any suitable technique. As an example, a negative mold of the body part may be made. The negative mold may then be used to form the positive physical model. One or more readily recognizable, optionally standardized symbols or other indicia may be placed at locations on the positive physical model where an orthosis or a prosthesis made using the positive physical model is to be modified (e.g., built up, etc.) in a manner prescribed by the health care professional ordering the orthosis, the prosthesis or another medical device. Once the positive physical model has been made, it may be scanned. Data obtained from scanning the positive physical model may then serve as a basis for the body model. Any indicia on the positive physical model may be transferred to the body model (e.g., for direction on subsequent modification to be made to a digital device model, etc.) or result in modification of the body model.

Regardless of how the body model is obtained or generated, it may be digitally applied to a digital device model, which may define various features of the custom orthosis, the custom prosthesis or another custom wearable and/or implantable medical device that will be made based on the body model. Non-limiting examples of such features include, but are not limited to, the outer periphery of the orthosis or the prosthesis, the general shape and/or contour of the orthosis or the prosthesis, uncustomized features of the orthosis or the prosthesis (e.g., outer surfaces that do not engage or contact the body part, etc.) and connectors for coupling the orthosis or orthosis part or the prosthesis or prosthesis part to other elements, among other features. When features, such as surface contours, dimensional positioning of two or more features of the body part with which the orthosis or the prosthesis will be used and the like, from the negative mold are applied to the digital device model, a customized digital model of the wearable and/or implantable medical device is created.

A body model and/or a digital device model may be modified to accommodate one or more features of a custom orthosis or a custom prosthesis that will be made on the basis of the respective digital device model. As an example, one or more portions of a surface of the body model or digital device model may be recessed so that an orthosis or a portion of an orthosis or a prosthesis or a portion of a prosthesis manufactured from the digital device model can accommodate one or more corresponding features (e.g., reinforcement elements, cushions or pads, etc.). As another example, one or more portions of the surface of the body model or the digital device model may be recessed to accommodate features of the body part, such as bony prominences, bony protrusions, or the like. In yet another example, one or more portions of the body model or the digital device model may be built up. By digitally building up one or more portions of the body model or digital device model, the body model or the digital device model may be modified to include one or more corresponding protruding features of a custom orthosis or a custom prosthesis. Such features may perform a variety of functions, including without limitation, support a corresponding portion of the body part, to apply a desired amount of pressure to a corresponding portion of the body part, and/or to facilitate proper alignment of a custom orthosis or a custom prosthesis with the body part, to identify only a few.

A surface of the body model or the digital device model may be modified to impart different regions of the surface and, optionally, different regions of a custom orthosis or a custom prosthesis that is to be fabricated on the basis of the body model or the digital device model, with different rigidities and/or flexibilities. The result of such further customization is a customized digital model of the wearable and/or implantable medical device (e.g., the orthosis, the prosthesis, etc.). Differences in the rigidities and/or flexibilities of different regions of a custom orthosis or a custom prosthesis may be achieved by using materials of different hardnesses in different regions of the custom orthosis or the custom prosthesis (e.g., softer materials in more flexible regions, harder materials in more rigid regions, etc.).

Once the customized digital device model has been generated and, if desired, modified, it may serve as the basis, or a three-dimensional blueprint, upon which additive manufacturing equipment (i.e., 3D printing equipment, such as fused deposition modeling (FDM) equipment, equipment for selective melting or sintering of granular material(s), etc.), relies to define a custom orthosis or a custom prosthesis, or at least a customized portion of an orthosis or a prosthesis. Generally, when operating under control of programming based on the customized digital device model, the additive manufacturing equipment may manufacture the custom orthosis or the custom prosthesis as a plurality of adjacent, adhered elements, or sections. The adjacent, adhered elements may be defined and associated with one another in a manner that physically represents the customized digital model. More specifically, the different elements of a custom orthosis or a custom prosthesis that is made by an additive manufacturing process may comprise layers that are at least partially superimposed with respect to one another.

A customized, form-fitting surface of a custom wearable and/or implantable medical device, such as a custom orthosis or a custom prosthesis, may have a contour that is defined by a plurality of adjacent, mutually adhered elements. In various embodiments, the adhered elements have dimensions that impart the finished product with a high degree of definition, including smooth surface contours. Adjacent adhered elements are also permitted to integrate with one another, which eliminates weak points in the finished structure (e.g., discrete boundaries between adjacent elements, etc.) and strengthens it.

Further customization may be achieved when additive manufacturing processes are used that provide for the use of two or more materials (e.g., different materials; materials with different properties, such as hardness or durometer, electrically insulative materials (e.g., plastics, elastomeric materials, etc.) and electrically conductive materials (e.g., metals, electrically conductive polymers, etc.), etc.) to define different regions of each element (e.g., layer, etc.). When such a process is used, one or more layers of a custom wearable and/or implantable medical device, such as a custom orthosis or a custom prosthesis, may include one or more rigid regions and one or more flexible regions, thus imparting the custom wearable and/or implantable medical device with a tailored pattern of rigid and flexible features. Without limiting the scope of this disclosure, rigid features may prevent or control unnatural or unwanted motion or movement (e.g., excessive movement beyond a normal range of motion, undesired movement between a residual body part and an interface of a prosthesis, etc.) while enabling a normal range of motion. More flexible features may provide for greater freedom of movement (e.g., for uninjured anatomical structures, for injured anatomical structures of the body part that are experiencing limited range or motion, to provide cushioning against a residual body part, etc.).

The custom wearable and/or implantable medical device (e.g., the custom orthosis, the custom prosthesis, etc.) resulting from an additive manufacturing process may then be assembled with other components of the orthosis or the prosthesis, if necessary, and used by the individual for whom it was made. The resulting custom wearable and/or implantable medical device may have substantially the same properties as, or even improved properties over, a hand-made custom wearable and/or implantable medical device (e.g., a hand-made custom orthosis, a hand-made custom prosthesis, etc.).

In addition to being useful for manufacturing customized portions of an orthosis or a prosthesis, techniques that incorporate teachings of this disclosure may be applied to the fabricating of other types of wearable and/or implantable medical devices. By way of non-limiting example, the disclosed processes may be used to fabricate splints and casts, including casts that enable use of a stabilized body part in water and, thus, from which water may be readily removed (i.e., the stabilized body part may be readily dried).

A system that incorporates teachings of this disclosure may include a physical model generation component and a custom manufacturing component. The physical model generation component may be the office of a health care provider who is prescribing and/or ordering a custom wearable and/or implantable medical device, such as a custom orthosis or a custom prosthesis, for a patient. The physical model generation component may provide (e.g., ship, etc.) the physical model to a custom manufacturing component (e.g., to a remote custom manufacturing component, etc.). Once the custom manufacturing component receives the physical model, it may manufacture the custom orthosis, the custom prosthesis or the other custom wearable and/or implantable medical device in accordance with the disclosed subject matter within a day or two. In total, this type of system may enable the manufacture of custom wearable and/or implantable medical devices within three days to five days.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 1 is a schematic representation of an embodiment of a method for generating a digital body model of a body part, which includes scanning the body part;

FIG. 2 is an impact curve obtained as a subject with an impaired foot walked on a treadmill;

DETAILED DESCRIPTION

Figure 3:
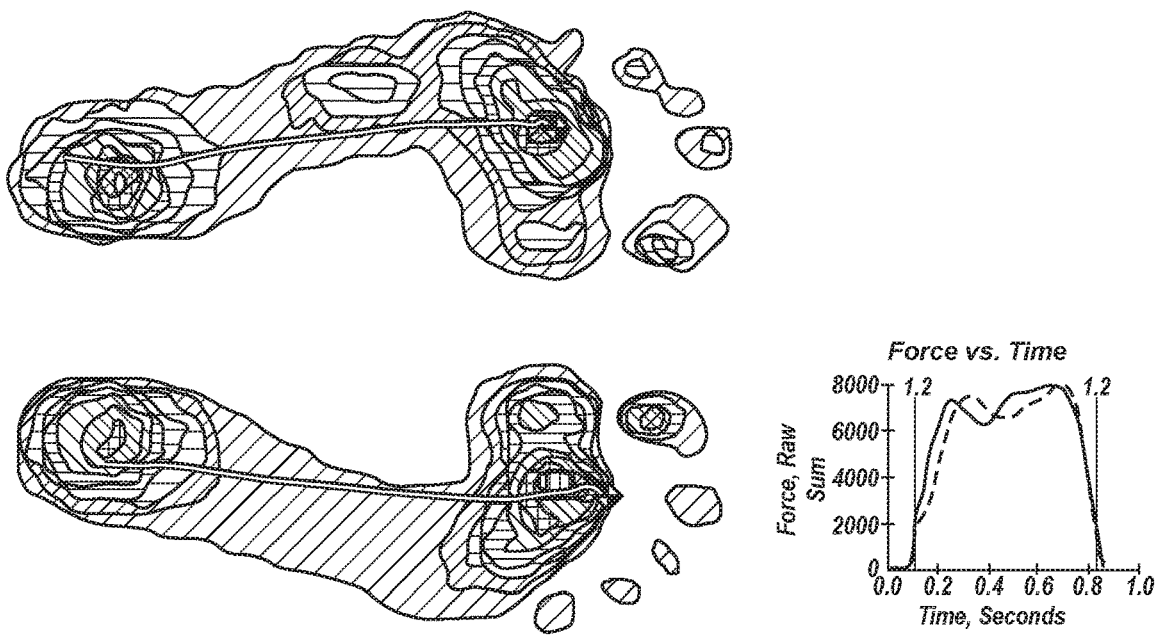
FIG. 3 is an impact force diagram of the forces experienced by the impaired foot as the subject walked on the treadmill.

In various embodiments, processes for making custom orthoses are disclosed and depicted. Although the disclosed embodiments relate to the manufacture of a custom foot bed for an ankle brace, processes that incorporate teachings of this disclosure may also be used to fabricate features of other types of orthoses, prostheses or other wearable and/or implantable medical devices that are custom-made for use with a body part of a particular individual, and in processes for making entire wearable and/or implantable medical devices. Accordingly, in addition to referring to orthoses, the term "custom orthosis," as used herein, may also apply to prostheses and to other wearable and/or implantable medical devices.

With reference to FIG. 1, an embodiment of a method for obtaining a model of a body part P is illustrated. While FIG. 1 depicts the body part P as being the sole of an individual's foot, this disclosure is applicable to a wide variety of body parts, including, without limitation, ankles, knees, wrists, elbows, residual limbs (following amputation, etc.), or other body parts that will interface with a wearable and/or implantable medical device, such as an orthosis or a prosthesis. In such a method, a scanner 10 that has been configured to generate a three-dimensional representation of a scanned object may be used to generate a three-dimensional digital representation of the body part P. In some embodiments, the scanner 10 may comprise a digitizer that operates based on a so-called "last," or basic representation (e.g., based on common dimensions for a particular demographic, etc.) of the body part P being digitized. A digitizer may include a probe, such as a faro arm, that obtains an outline of the body part P at intermittent locations along the body part P (e.g., every centimeter, every inch, etc.). These outlines, which provide cross-sections of the body part P, may then be assembled, and data interpolated therebetween, to provide a three-dimensional model of the body part P. In other embodiments, the scanner 10 may comprise a three-dimensional scanner of a known type.

The scanner 10 may be configured to obtain a single image of the body part P, or it may be configured to obtain two or more images of the body part P in a corresponding number of positions. A scanner 10 that obtains data while a body part P remains stationary may be used for this purpose by positioning the body part P in a plurality of different, substantially stationary positions while the scanner 10 operates. Alternatively, the scanner 10 may be configured to obtain data on a body part P as the body part P is in motion (e.g., a foot, ankle and/or knee as a subject walks or runs on a treadmill, a residual limb within a socket of a prosthesis during movement of the residual limb and the prosthesis, etc.). Some specific, but non-limiting embodiments of such a scanner include one or more fluoroscopes or similar devices that obtain multiple images during movement, motion capture equipment, and the like. Of course, other apparatuses that provide data that may be used to generate a three-dimensional model may also be employed as the scanner 10.

The scanner 10 may transmit data 12 obtained from scanning the body part P to a processing element 14, such as a computer processor. The processing element 14, under control of one or more programs, may generate a digital, three-dimensional, model of the body part P, or "digital body model" 16 or "body model." The digital body model 16 may include data 12 that represents one or more surfaces 18 that are contoured and arranged complementarily to, or as negatives of, one or more corresponding surfaces of the body part P. The one or more surfaces 18 of the digital body model 16 may represent surface contours that will ultimately be included in a custom orthosis.

In embodiments where the data 12 obtained by the scanner 10 corresponds to two or more chronological positions of the body part P, the data 12 may provide additional insight as to the specific anatomical cause or causes of any impairment of the body part P. Such data 12 may be compared with other data 12 on the body part P. As a non-limiting example, data 12 obtained during a plurality of scans of a foot in motion throughout gait, which data 12 corresponds to the anatomy of the foot throughout gait, may be compared with other data 12 (e.g., an impact curve (see FIG. 2), an impact force diagram (see FIG. 3), etc.) obtained as the subject walks or runs. Abnormalities in such other data (e.g., differences from normal movement, undesirable events, etc.) may be useful in identifying a specific anatomical cause or causes of each abnormality. Each anatomical cause may then be addressed while generating the digital body model 16. Accordingly, the digital body model 16 may account for the dynamic range of the body part P.

Figure 4:
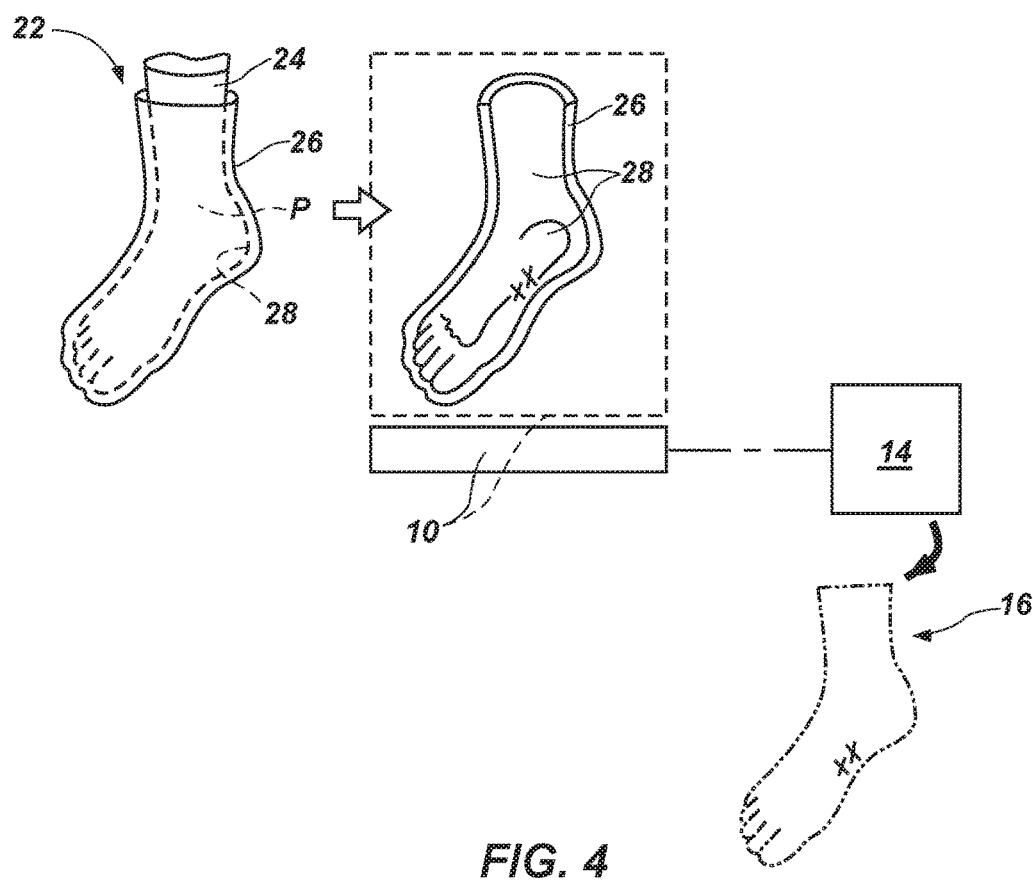
FIG. 4 is a schematic representation of another embodiment of a method for generating a digital body model of a body part, in which a physical body mold, or cast, is formed, then scanned.

As an alternative to directly scanning a body part P to generate a digital body model 16, a digital body model 16 may be obtained from a physical negative model, or mold 26, of the body part P, as illustrated by FIG. 4. A variety of processes may be used to make one or more physical negative models 22 of the body part P. Without limitation, such a method may include positioning a thin, form-fitting element 24 over the body part P. A mold 26 (e.g., a cast, such as a plaster cast, a fiberglass cast, etc.) may then be built up on the form-fitting element 24 and around the body part P in a manner that causes an inner surface 28 to substantially assume the shape of the body part P. In some embodiments, the mold 26 may be built up without deforming the shape of the body part P or any of its surfaces. Once the mold 26 has hardened, it may be removed (e.g., from the body part P, etc.).

Once the mold 26 has been removed from a body part P for which an orthosis, such as an ankle brace, a prosthesis, or another wearable and/or implantable medical device is being customized, the mold 26 may function as a physical negative model of the body part P. More specifically, the mold 26, in one or more sections, may be scanned by a scanner 10 to obtain digital data representative of the mold 26, and that data may be processed by a processing element 14, which may then generate a digital, three-dimensional model 16, or "digital body model" 16 or "body model," of the body part P or portion thereof.

Figure 5:
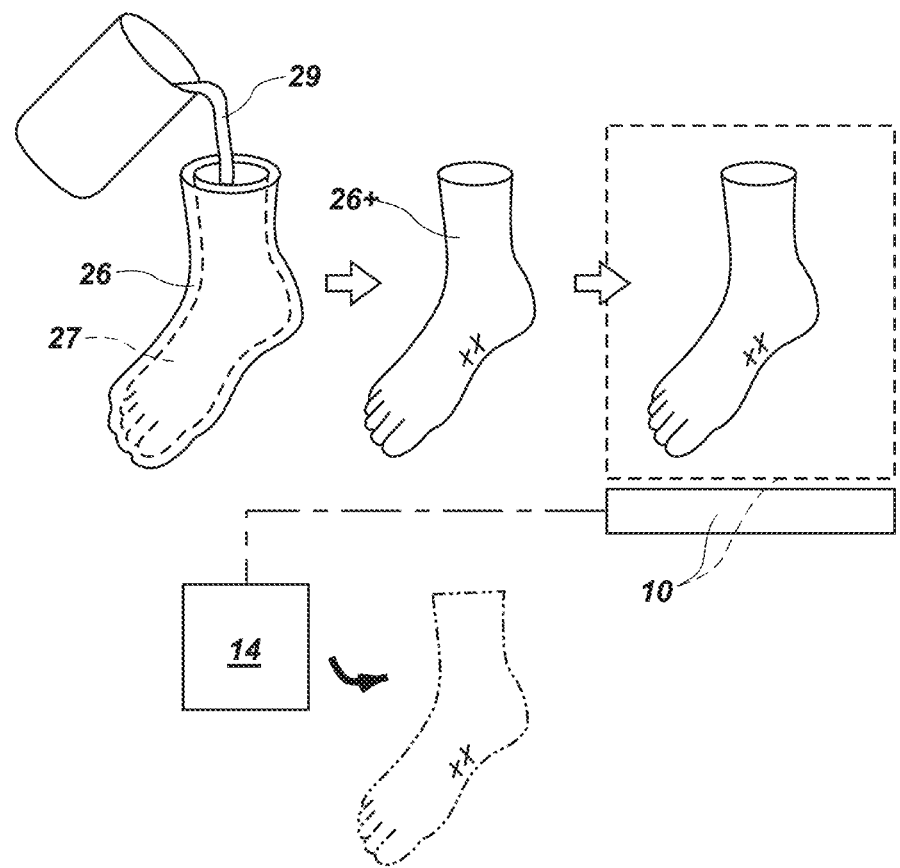
FIG. 5 is a schematic representation of yet another embodiment of a method for generating a digital body model of a body part, in which a mold, or cast, is formed, then used to form a positive physical model, which is then scanned.

FIG. 5 is a schematic representation of a process in which a mold 26 of a body part P is formed, as described in reference to FIG. 4, and then the mold 26 used to form a positive physical model 26+ of the body part P. The positive physical model 26+ may be formed in any suitable manner known in the art. Without limitation, a flowable, hardenable material 29 (e.g., a liquid resin, plaster, etc.) may be introduced into a cavity 27 of the mold 26. As the flowable, hardenable material 29 solidifies, it forms the positive physical model 26+, and the mold 26 may be removed from the positive physical model 26+. The positive physical model 26+ may then be scanned, and the data obtained from scanning may be used to generate a digital body model 16 of the body part P or a portion thereof.

In various embodiments, one or more modification symbols X may be used on a mold 26, a positive physical model 26+, and/or a digital body model 16 to identify regions of an orthosis, a prosthesis, or another wearable and/or implantable medical device that are to be modified in a manner that differs from the contour of a portion of a body part P with which the wearable and/or implantable medical device is to be used. A modification symbol X may comprise a readily recognizable, even standardized, indicia that enables an individual (manually) or a computer (automatically) to identify the manner (e.g., location(s), extent(s), etc.) to which a wearable and/or implantable medical device is to be modified (e.g., areas that are to be built up, areas that are to be formed from a material with a hardness that differs from a hardness of a remainder of the wearable and/or implantable medical device, recessed areas, etc.). The modification that corresponds to a particular modification symbol X may be transferred to the digital body model 16 for subsequent use, or the modification that corresponds to that modification symbol X may be incorporated into the digital body model 16 (i.e., the digital body model 16 may be modified). The modification symbol X may signal to an individual that certain modifications are to be made to the digital body model 16 or to the digital device model 30 (see FIG. 6), and the individual may manually make a modification that corresponds to each modification symbol X. Alternatively, each modification symbol X may be configured to be recognized by a processing element that generates the digital body model 16 or applies the digital body model 16 to the digital device model 30, and the processing element may incorporate the appropriate modification into the digital body model 16 or to the digital device model 30.

Figure 6:
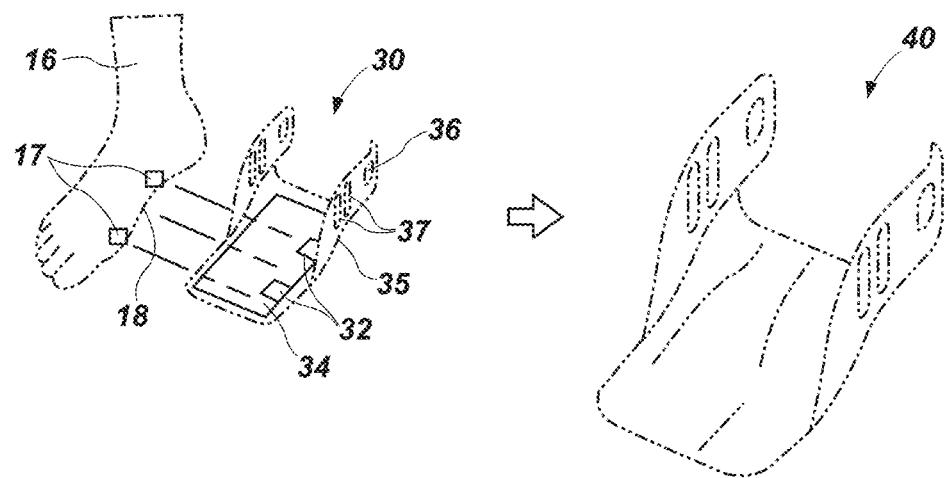
FIG. 6 provides a representation of application of a digital body model to a device model to generate a digital custom device model.

Turning now to FIG. 6, once a digital body model 16 of an individual's body part P has been generated (and regardless of the manner in which digital body model 16 was generated), the digital body model 16 may be applied to (e.g., overlaid with, etc.) a digital device model 30 (e.g., by processing element 14, another processing element, etc.). The digital device model 30 may include a customizable portion 34, as well as standard features, such as the outer periphery 35, one or more coupling elements 36 (e.g., hinge elements, etc.) and one or more stiffening features 37 (e.g., the illustrated gussets, etc.) of the illustrated orthosis, standard features of a prosthesis (e.g., a prosthetic limb, etc.), or standard features of any other wearable and/or implantable medical device, among other standard features.

In a specific embodiment, the digital body model 16 may be applied to the digital device model 30 by identifying two or more features 17 on the digital body model 16 that correspond to predetermined reference features 32 on a digital device model 30. The corresponding features 17 and 32 may then be aligned with one another, effectively superimposing the digital body model 16 over at least a customizable portion 34 of the digital device model 30. Any data from the digital body model 16 located outside the customizable portion 34 of the digital device model 30 may be discarded. The remaining data from the digital body model 16, including data representative the of one or more surfaces 18 that complement, or are negatives, of surfaces of the body part P for which a custom orthosis is being manufactured, may be applied to a customizable portion 34 of the digital device model 30 (i.e., it may be incorporated into the digital device model 30 to define a customized digital model 40.

Figure 7:
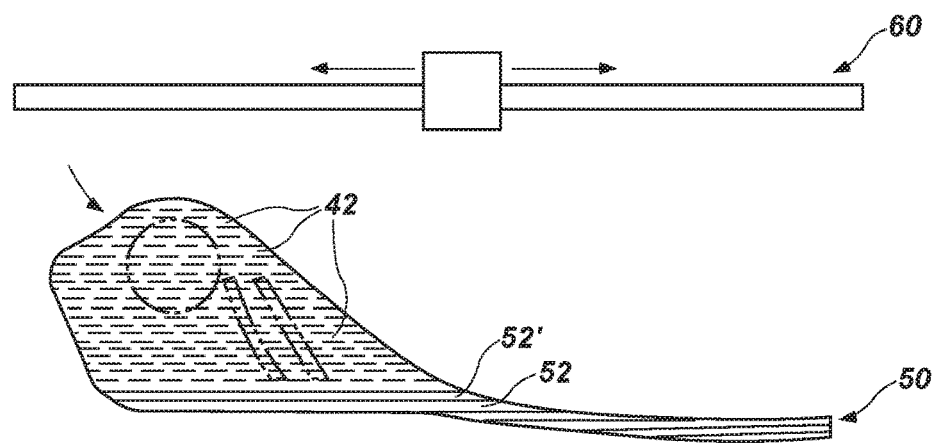
FIG. 7 illustrates an embodiment of a process in which a digital custom device model provides a pattern for fabrication of a custom wearable and/or implantable medical device, such as the depicted orthosis or a prosthesis, in which an additive manufacturing process is used to make a custom wearable and/or implantable medical device.

Once a customized digital model 40 has been generated, it may be processed and used to form a custom wearable and/or implantable medical device 50 (FIG. 7), or at least a portion of a custom wearable and/or implantable medical device 50. FIG. 7 schematically illustrates an embodiment of a method for manufacturing, or fabricating, a custom wearable and/or implantable medical device 50 from a customized digital model 40. As an example of such a method, an additive manufacturing process, such as that effected by the systems available from Objet Geometries, Ltd., of Rehovot, Israel, may be used to fabricate some or all of the custom wearable and/or implantable medical device 50 as a series of layers. When such a process is used, the customized model 40 may be separated into a plurality of sections 42, such as slices or layers (e.g., the customized digital model 40 may be converted from a CAD (Computer Aided Design) format to any suitable format, such as an STL (STereoLithography) format, etc.).

Each of the sections 42 of the customized digital model 40 may be used by an additive manufacturing system 60 to define a corresponding section 52 of a custom wearable and/or implantable medical device 50. More specifically, the additive manufacturing system 60 may be used to fabricate the custom wearable and/or implantable medical device 50, as well as any contoured surfaces that are intended to fit to the form, or contour, of a body part P (FIGS. 1 and 4), one section 52 (e.g., layer, etc.) at a time. As each section 52 is formed, the material from which it is formed may cure or otherwise solidify. Once a section 52 has at least partially solidified (e.g., before that section 52 has fully cured, etc.), a subsequent section 52' may be formed adjacent to it (e.g., at least partially superimposed over it, etc.). The subsequent section 52' may be formed before the previously formed, adjacent section 52 has fully cured, enabling at least some integration between the adjacent sections 52 and 52', which may impart a custom wearable and/or implantable medical device 50 that results from such a process with substantially smooth surfaces, increase the fracture resistance (and, optionally, the flexibility) of the custom wearable and/or implantable medical device 50, increase the strength of the custom wearable and/or implantable medical device 50, otherwise improve the custom orthosis, or provide any combination of the foregoing. Alternatively, one section 52 may substantially cure or fully cure before the subsequent section 52' is formed, resulting in a structure with a discernable, discrete boundary between the adjacent sections 52 and 52'. In either event, the resulting structure includes a plurality of adjacent, mutually adhered sections 52 (e.g., a plurality of at least partially superimposed, mutually adhered layers, etc.). Such a process may be used to form a customized portion of the custom wearable and/or implantable medical device 50, an entire part of the custom wearable and/or implantable medical device 50, or the entire custom wearable and/or implantable medical device 50.

When the additive manufacturing system 60 includes a so-called "3D printer," such as that manufactured by Objet, and a polypropylene-like material, such as the DurusWhite™ material available from Objet, is used to form at least a portion of the custom wearable and/or implantable medical device 50, each section 52 (e.g., layer, etc.), may have a thickness of about 0.005 inch to about 0.001 inch or less. The smoothness of the surfaces of the custom wearable and/or implantable medical device 50 corresponds, at least in part, to the thinness of the sections 52 from which the custom wearable and/or implantable medical device 50 is formed, with thinner sections 52 forming smoother surfaces.

In some embodiments, two or more materials (e.g., different materials; a material without additives and the same material with additives; the same material with different additives; etc.) may be co-deposited (e.g., as part of the same layer 52, as different layers 52, as combinations of the foregoing, etc.) to form at least part of a custom wearable and/or implantable medical device 50. The materials that are used in additive manufacturing processes may include additive manufacturing materials that are currently available (depending, of course, upon the additive manufacturing technique and equipment that are employed), as well as other suitable additive manufacturing materials (including, but not limited to, those currently under development). In some embodiments, one or more supplements may be included in an additive manufacturing material; the supplement(s) may impart the additive manufacturing material with one or more desired properties. Without limitation, an additive manufacturing material may include a supplement that may impart the additive manufacturing material with further strength (e.g., carbon fiber, carbon nanotubes, etc.). As another example, a supplement may impart an additive manufacturing material with electrical conductivity (e.g., carbon nanotubes, graphene, electrically conductive carbon black, metallic filaments, etc.). The thermal conductivity of an additive manufacturing material may also be tailored with supplements (e.g., ceramic microspheres, ceramic particles, boron nitride particles, silica microspheres, silica particles, etc.). As yet another example, a supplement may reduce the density of an additive manufacturing material (e.g., hollow microspheres, such as polymeric microspheres or glass microspheres; etc.).

Figure 8:
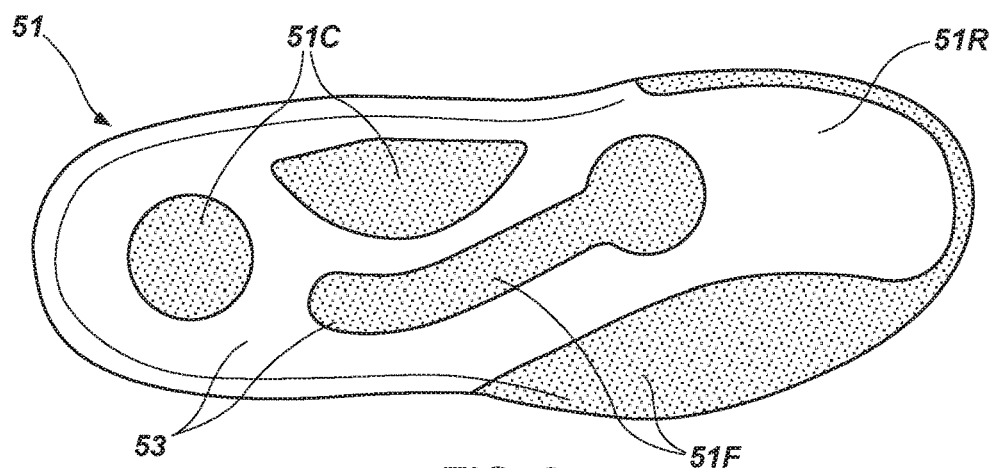
FIG. 8 illustrates an embodiment of a part of a custom wearable and/or implantable medical device fabricated in accordance with the method depicted by FIG. 7 and including at least one layer with at least one rigid region and at least one flexible region, which define rigid and flexible regions of the part.

As an example of the use of different materials to form a custom wearable and/or implantable medical device 50, a majority of the custom wearable and/or implantable medical device 50 may be fabricated from a material that imparts the custom wearable and/or implantable medical device 50 with one or more desired characteristics (e.g., rigidity, durability, etc.), while another material may form a coating on at least part of the custom wearable and/or implantable medical device 50 to provide it with added characteristics (e.g., flexibility, cushioning, etc.). FIG. 8 shows a specific embodiment of part of a custom wearable and/or implantable medical device 50 (FIG. 7) in which each of one or more layers 52 (FIG. 7) (e.g., a layer 52 that forms a surface of the part, a plurality of layers 52 adjacent to a surface of the part, etc.) is defined from two or more materials with different characteristics. More specifically, FIG. 8 illustrates an embodiment of a foot bed 51 of a foot and/or ankle embodiment of a custom wearable and/or implantable medical device 50, with a rigid region 51R and a plurality of flexible regions 51F. More specifically, the rigid region 51R may be defined by a material having a hardness of about 90 Shore A or greater durometer, while the flexible regions 51F may have a hardness of about 30 Shore A to about 40 Shore A. In addition, the foot bed 51 includes cushions 51C, which may comprise an integral part of one or more layers 52 of the foot bed 51, or which may be applied to a surface 53 of the foot bed 51. The embodiment of foot bed 51 illustrated by FIG. 8 includes an elongated, curved flexible region 51F that generally follows the path of the fundamental longitudinal arch of the foot, and a lateral flexible region 51F located beneath the fifth metatarsal (i.e., the small toe, or "pinkie toe"). The curved flexible region 51F may allow the foot to flex where it naturally wants to flex. The lateral flexible region 51F may provide for flexibility in the mid-stance and toe-off phases of a subject's gait. A portion of the rigid region 51R adjacent to the curved flexible region 51F may define an arch support that prevents the arch of the foot from collapsing. Cushions 51C may be provided on the arch support and beneath the heel for comfort.

As another example, a first material may be used to form layers 52 or other adhered elements of a majority of the custom wearable and/or implantable medical device 50, while a second material (e.g., a softer material, etc.) may be used to form a plurality of adjacent, mutually adhered layers 52 or other elements that define features (e.g., cushioned areas, etc.) of the custom wearable and/or implantable medical device 50. Such an arrangement may be useful in the interface components (e.g., sockets, etc.) of prostheses, where the softer material(s) provide(s) for cushioning and/or comfort for a residual body part, while the harder material(s) impart(s) the interface component with support and stability.

In embodiments wherein the custom wearable and/or implantable medical device 50 comprises only part of a custom wearable and/or implantable medical device, the custom wearable and/or implantable medical device 50 may be assembled with one or more standard elements of the custom wearable and/or implantable medical device 50.

A system according to this disclosure may include a three-dimensional scanner 10, at least one processing element 14 and an additive manufacturing system 60, which may perform the above-disclosed functions. Additionally, such a system may include a component in which a cast, or negative model, of a body part P (FIG. 1) is obtained, as well as an assembly component, in which a custom wearable and/or implantable medical device 50 may be assembled with one or more standard elements of the custom wearable and/or implantable medical device 50 to define a complete custom wearable and/or implantable medical device 50.

When additive manufacturing processes are used to fabricate a custom wearable and/or implantable medical device 50, the labor-intensive processes of hand-forming a positive model and making the custom wearable and/or implantable medical device 50 may be eliminated. Thus, the amount of time it takes to make a custom wearable and/or implantable medical device 50 may be significantly reduced. In some embodiments, it may be possible to reduce the time it takes to make a custom wearable and/or implantable medical device 50 from two weeks or more to as little as three to five days.

Figure 9:
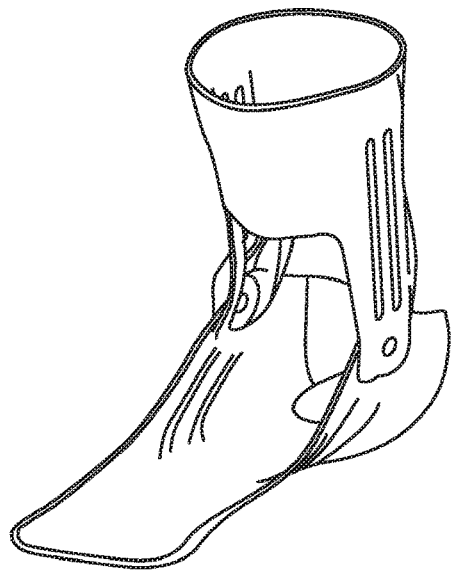
FIG. 9 shows an embodiment of a custom wearable and/or implantable medical device.

In a specific embodiment, the foregoing processes may be used to form one or more surfaces of an ankle brace, such as that depicted by FIG. 9. The embodiment of ankle brace depicted by FIG. 9 includes an upper element, which is configured to be positioned around and ankle and to hold the ankle brace in place, and a bottom element that comprises the embodiment of custom wearable and/or implantable medical device 50 shown in FIGS. 6 and 7. In some embodiments, the upper element may comprise an off-the-shelf component that may have a standard shape and one of a limited number of (e.g., one, three, five, etc.) standard sizes. The use of one or more standard components in the manufacture of a custom (or at least partially custom) wearable and/or implantable medical device 50 may decrease the amount of time required to make the custom wearable and/or implantable medical device 50 and minimize the cost of a custom wearable and/or implantable medical device 50. In other embodiments, however, the disclosed processes may be used to fabricate two or more components of a custom wearable and/or implantable medical device 50, such as both the upper element and the lower element of the depicted ankle brace.

Custom components of wearable and/or implantable medical devices may be desirable in a variety of situations, including those where a standard component will not fit a particular body part (e.g., the contour on the bottom of a foot, etc.) in a desired manner, and cannot be adjusted in a manner that will provide the desired fit.

Although the foregoing description contains many specifics, these should not be construed as limiting the scopes of the inventions recited by any of the appended claims, but merely as providing information pertinent to some specific embodiments that may fall within the scopes of the appended claims. Features from different embodiments may be employed in combination. In addition, other embodiments may also lie within the scopes of the appended claims. All additions to, deletions from and modifications of the disclosed subject matter that fall within the scopes of the claims are to be embraced by the claims.

What is claimed:

1. A method for fabricating a custom wearable and/or implantable medical device, comprising:
   obtaining a plurality of scans of a body part for which the custom wearable and/or implantable medical device is to be made, the plurality of scans corresponding to a plurality of positions of the body part during movement of the body part or during movement of an adjacent body part;
   generating a digital body model of the body part from the plurality of scans, the digital body model including custom surface data corresponding to at least one surface of the body part;
   applying the digital body model to a digital device model to incorporate the custom surface data into the digital device model to create a custom digital device model; and
   using the custom digital device model to manufacture the custom wearable and/or implantable medical device for use on the body part.

2. The method of claim 1, wherein applying the digital body model to the digital device model comprises applying the digital body model to a digital device model including at least one standard feature.

3. The method of claim 2, wherein applying the digital body model to the digital device model comprises incorporating custom surface data into a customizable area of the digital device model.

4. The method of claim 1, further comprising:
   analyzing data from the plurality of scans to identify at least one location of the body part that is subject to unnaturally restricted motion during movement of the body part; and
   fabricating the custom wearable and/or implantable medical device to:
     enable natural movement of the at least one location of the body part.

5. The method of claim 1, wherein obtaining the plurality of scans comprises:
   forming a plurality of molds of the body part in a plurality of different positions, each mold of the plurality of molds corresponding to a position of the plurality of different positions; and
   scanning the plurality of molds to provide the custom surface data for generating the digital body model.

6. The method of claim 1, further comprising:
forming a plurality of molds of the body part in a plurality of different positions, each mold of the plurality of molds corresponding to a position of the plurality of different positions;
forming a plurality of positive physical models of the body part, each positive physical model of the plurality of positive physical models being made from a mold of the plurality of molds; and
scanning the plurality of positive physical models to provide the custom surface data for generating the digital body model.

7. The method of claim 1, further comprising:
applying at least one modification symbol to the digital body model; and
incorporating a modification corresponding to the at least one modification symbol into the digital body model, the at least one modification symbol corresponding to a modification to be made while manufacturing the custom wearable and/or implantable medical device.

8. The method of claim 1, wherein using the custom digital device model to manufacture the custom wearable and/or implantable medical device for use on the body part includes:
analyzing data from the plurality of scans to identify at least one location of the body part that is subject to undesired motion or movement during movement of the body part; and
manufacturing the custom wearable and/or implantable medical device to:
prevent the undesired motion or movement of the at least one location of the body part; and
enable natural movement of unaffected locations of the body part.

9. The method of claim 1, wherein using the custom digital device model includes:
separating the custom digital device model into a plurality of sections; and
sequentially defining a plurality of adjacent sections of the custom wearable and/or implantable medical device, at least one section being formed adjacent to and secured to a previously formed section of the custom wearable and/or implantable medical device.

10. The method of claim 1, wherein using the custom digital device model to manufacture the custom wearable and/or implantable medical device for use on the body part includes:
defining a first region of the custom wearable and/or implantable medical device from a first material; and
defining a second region of the custom wearable and/or implantable medical device from a second material, the second material being different from the first material, the second region being in a same plane as the first region.

11. The method of claim 1, wherein fabricating the custom wearable and/or implantable medical device comprises fabricating a custom prosthesis.

12. The method of claim 1, wherein obtaining the plurality of scans comprises dynamically scanning the body part for which the custom wearable and/or implantable medical device is to be made during movement of the body part and/or during movement of an adjacent body part.

13. A method for manufacturing a custom wearable and/or implantable medical device, comprising:
obtaining surface contour data corresponding to a contour of at least one surface of a body part of a patient;
applying the surface contour data to a digital device model to define a custom digital device model; and
fabricating the custom wearable and/or implantable medical device by selectively using a plurality of different materials in an additive manufacturing process.

14. The method of claim 13, further comprising:
generating a physical model of the body part of the patient,
wherein obtaining the surface contour data comprises scanning the physical model.

15. The method of claim 14, wherein generating the physical model is conducted remotely from fabricating the custom wearable and/or implantable medical device.

16. The method of claim 13, comprising defining a custom interface of a prosthesis, including at least one cushioning region and at least one support and/or stability region.

17. A method for manufacturing a custom wearable and/or implantable medical device, comprising:
generating a physical model of a body part of a patient; and
obtaining surface contour data corresponding to a contour of at least one surface of the body part from the physical model;
applying the surface contour data to a digital device model to define a custom digital device model; and
using the custom digital device model to fabricate the custom wearable and/or implantable medical device.

18. The method of claim 17, wherein using the custom digital device model to fabricate the custom wearable and/or implantable medical device comprises using the digital device model in an additive manufacturing process.

19. The method of claim 17, further comprising:
assembling a custom element of the custom wearable and/or implantable medical device with at least one standard element of the custom wearable and/or implantable medical device.

20. The method of claim 17, wherein using the custom digital device model to fabricate the custom wearable and/or implantable medical device comprises fabricating the custom wearable and/or implantable medical device within a day.

* * * * *